(12) United States Patent
Dorenkamp et al.

(10) Patent No.: US 7,673,546 B2
(45) Date of Patent: Mar. 9, 2010

(54) MICROTOME HAVING A COOLING DEVICE

(75) Inventors: Claudia Dorenkamp, Mühlhausen (DE); Stefan Künkel, Karlsruhe (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 267 days.

(21) Appl. No.: 11/610,555

(22) Filed: Dec. 14, 2006

(65) Prior Publication Data

US 2007/0137451 A1    Jun. 21, 2007

(30) Foreign Application Priority Data

Dec. 17, 2005    (DE) .................. 20 2005 019 765 U

(51) Int. Cl.
*G01N 1/06* (2006.01)
(52) U.S. Cl. ...................... 83/170; 83/915.5
(58) Field of Classification Search ............. 83/955.5, 83/915.5, 170, 171, 15; 62/320, 341, 51.1
See application file for complete search history.

(56) References Cited

U.S. PATENT DOCUMENTS 3,218,896 A * 11/1965 McCormick ................. 83/15
3,220,290 A * 11/1965 Shandon ..................... 83/171
3,296,821 A *  1/1967 Malinin ..................... 62/320
3,447,594 A *  6/1969 Andrews .................... 165/263
5,711,200 A    1/1998 Thiem
5,960,640 A * 10/1999 Teppke ...................... 62/320
7,210,306 B2 * 5/2007 Heid et al. .................. 62/320

FOREIGN PATENT DOCUMENTS

DE       9421559 U1    2/1996

OTHER PUBLICATIONS

Ernst Leitz Wetzlar GmbH, Wetzlar, Germany: Instruction Manual entitled "Leitz 1512 Rotationsmikrotome"; Apr. 1981.

* cited by examiner

*Primary Examiner*—Stephen Choi
(74) *Attorney, Agent, or Firm*—Hodgson Russ LLP

(57) ABSTRACT

A microtome (1), having a knife (9) for sectioning a specimen (5) for subsequent microscopic examination, is described. The microtome (1) comprises a cooled specimen holder (2) for receiving the specimen (5), the specimen holder (2) being connected to a coolant circuit (3). Additionally associated with the specimen holder (2) is a cooled thermal conduction plate (4) that can be placed over the specimen (5).

12 Claims, 3 Drawing Sheets

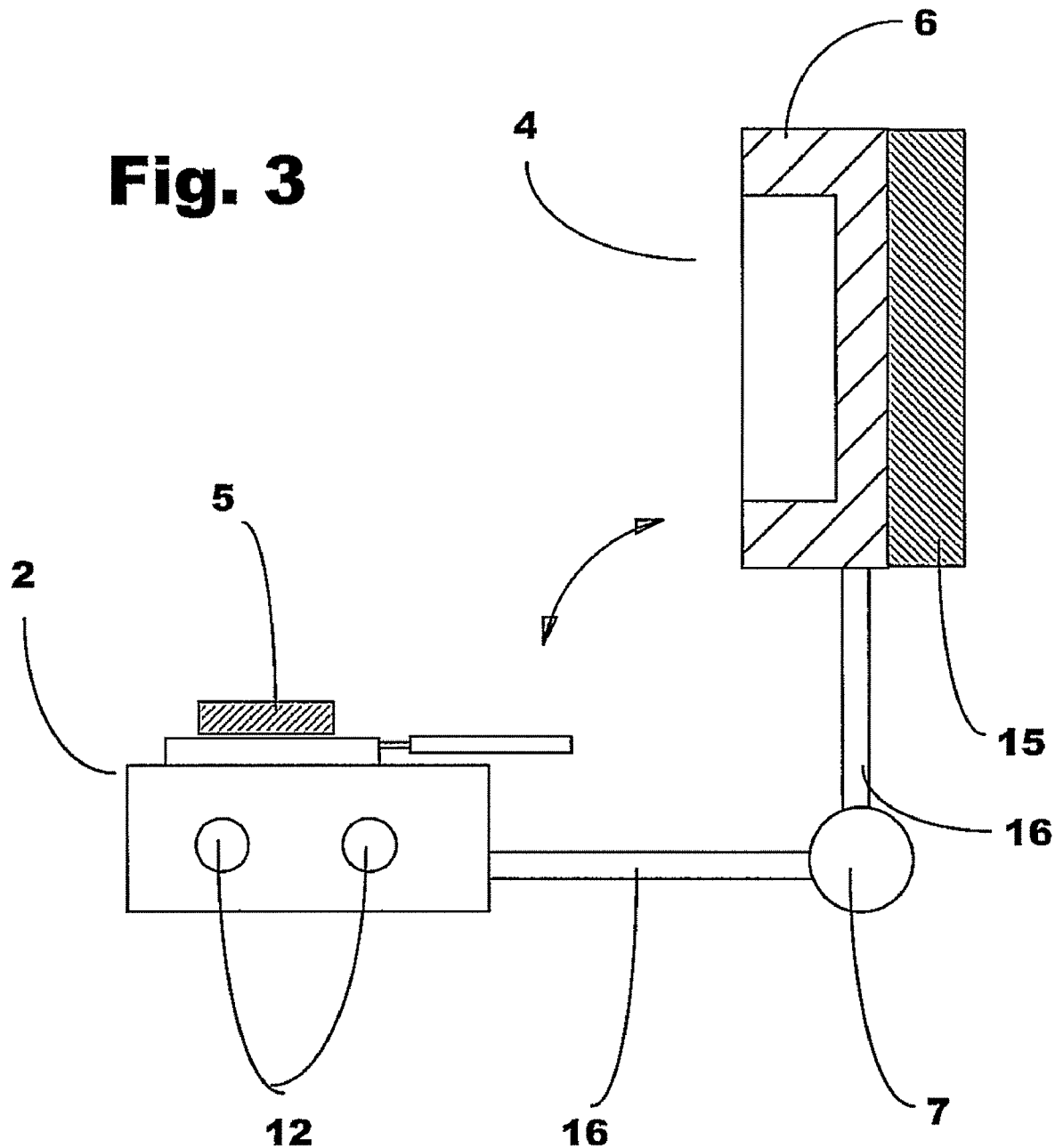

MICROTOME HAVING A COOLING DEVICE

CROSS REFERENCE TO RELATED APPLICATIONS

This application claims priority of the German utility application 20 2005 019 765.3 filed Dec. 17, 2005, which is incorporated by reference herein.

FIELD OF THE INVENTION

The present invention relates to a microtome for sectioning specimens for subsequent microscopic examination, having a cooled specimen holder.

BACKGROUND OF THE INVENTION

Microtomes for sectioning frozen or cooled specimens comprise a special cooling device. The samples to be sectioned are cooled, in this context, to a specific predetermined temperature. The temperatures are as a rule between −10° C. and −50° C. To ensure a constant temperature, either the microtomes are arranged in complexly encapsulated cryostat chambers and the latter are appropriately cooled, or separate refrigeration devices are provided that can be attached to the microtome. A microtome having a cryostat chamber and a refrigeration device is presented, for example, in DE 44 34 937 C1 and its counterpart U.S. Pat. No. 5,711,200. In this document, the entire cryostat chamber is cooled by way of the refrigeration device.

A temperature regulating device for the specimen receptacle in a cryostat microtome is disclosed in DE 94 21 559 U1. Associated with the specimen receptacle is a specimen head on which the specimen to be sectioned can be mounted. The specimen receptacle is equipped with cooling hoses for cooling the specimen head and the specimen.

The company document "LEITZ 1512 Rotationsmikrotom, Anleitung, Liste [Rotary microtome, instructions, list] 311.530-047, April 1981, Ernst Leitz Wetzlar GmbH" discloses a microtome (Leitz 1512) having an attachable, separate "Kryomat 1700" cooling unit. Here a freezing chamber having a coolant connector hose is mounted in the specimen clamp of the microtome. The specimen stages with the samples are slid onto the freezing chamber and cooled there.

The above-described devices for sectioning cooled or frozen samples have proven successful in practical use.

With very thick specimens or specimens embedded in paraffin, however, it has been found that the heat generated by the sectioning operation at the surface of the specimen cannot be dissipated quickly enough. The result is that the sample begins to thaw in the region of the sectioned surface, and the sectioning temperature is thus no longer optimal. For this reason, in practical use the specimens are removed from the specimen receptacle and brought back to the requisite temperature on separate cooling plates. This procedure is of course very time-consuming, since each specimen change necessitates a realignment of the specimen with respect to the knife edge.

SUMMARY OF THE INVENTION

It is therefore an object of the present invention to minimize the time expenditure when sectioning cooled or frozen samples.

This object is achieved, according to the present invention, by the features described herein. Further advantageous developments of the invention are the subject matter of the dependent claims.

The invention is notable for the fact that the specimen holder additionally has associated with it a cooled thermal conduction plate that can be placed as necessary in front of the specimen and thus additionally cools the sectioned surface of the specimen. Optimum heat transport from the precut surface to the thermal conduction plate is thus achieved without laborious removal of the specimen from the specimen retainer.

In a development of the invention, the thermal conduction plate is connected directly to the coolant circuit, so as thereby to eliminate any additional cooling complexity. It is of course also possible to connect the thermal conduction plate to its own coolant circuit.

In a further embodiment of the invention, a frame having a heat absorber is associated with the thermal conduction plate. The dimensions of the thermal conduction plate are usually adapted to the paraffin blocks being used, so that the thermal conduction plate can cover the surface of the paraffin block.

In a development of the invention, the thermal conduction plate is preferably has a round or rectangular shape so that paraffin blocks which are round or rectangular in cross-sectional shape are effectively cooled.

In a further embodiment of the invention, the thermal conduction plate and/or the frame is manufactured from a highly thermally conductive material, preferably metal. The use of chrome-plated brass not only ensures good thermal conductivity, but also guarantees very good corrosion resistance.

In a development of the invention, the thermal conduction plate is arranged on the microtome or the specimen holder pivotably via a joint. It is thus possible to work quickly without laborious modification to the microtome.

In a further embodiment of the invention, the thermal conduction plate is connected via a coolant hose directly to the specimen holder, so that the existing coolant circuit is additionally usable and only short hose connections between the specimen holder and the thermal conduction plate are necessary.

In a development of the invention, the coolant circuit is connected to the coolant circuit of a refrigeration device of a cryostat. The apparatus having the thermal conduction plate can be used as an additional unit both on a microtome and on a cryostat microtome.

In a further embodiment of the invention, the thermal conduction plate is embodied as a Peltier element or is connected to a Peltier element. Electrically operating cooling for the specimen is thereby achieved in simple fashion, so that connection of the thermal conduction plate to the coolant circuit can be dispensed with.

BRIEF DESCRIPTION OF THE DRAWINGS

The invention will be explained in more detail with reference to two exemplifying embodiments, with the aid of the schematic drawings in which:

FIG. 3 is a view of the specimen holder with a thermal conduction plate and Peltier element.

DETAILED DESCRIPTION OF THE INVENTION

Figure 1:
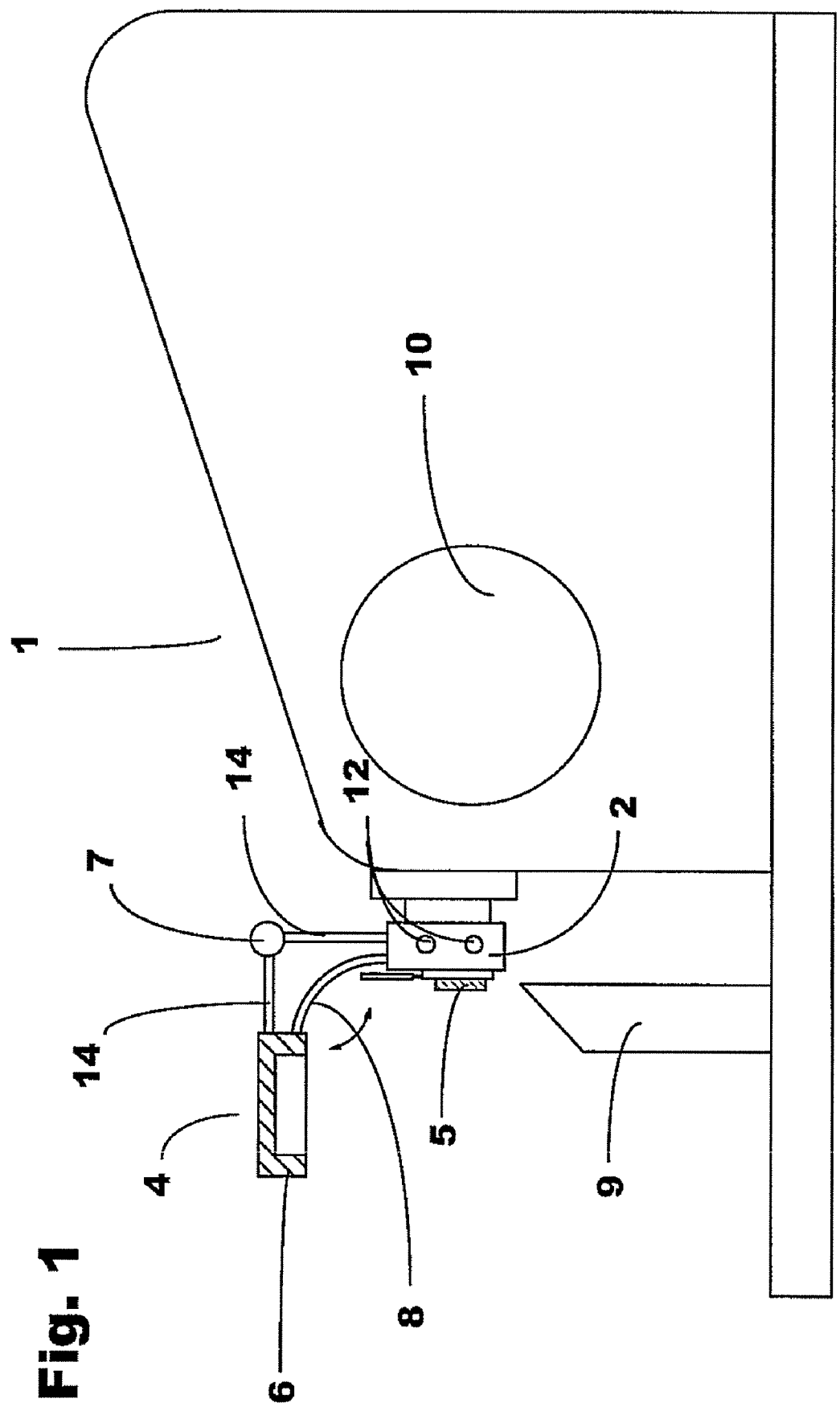
FIG. 1 is a view of the microtome with a specimen holder and thermal conduction plate.

FIG. 1 is a view of a microtome 1 having a knife 9, having a drive device 10 for a specimen holder 2 on which is arranged a specimen 5 to be sectioned. By way of drive device 10 a relative motion can be produced between specimen holder 2 and sectioning knife 9, and a cut can thus be made.

Figure 2:
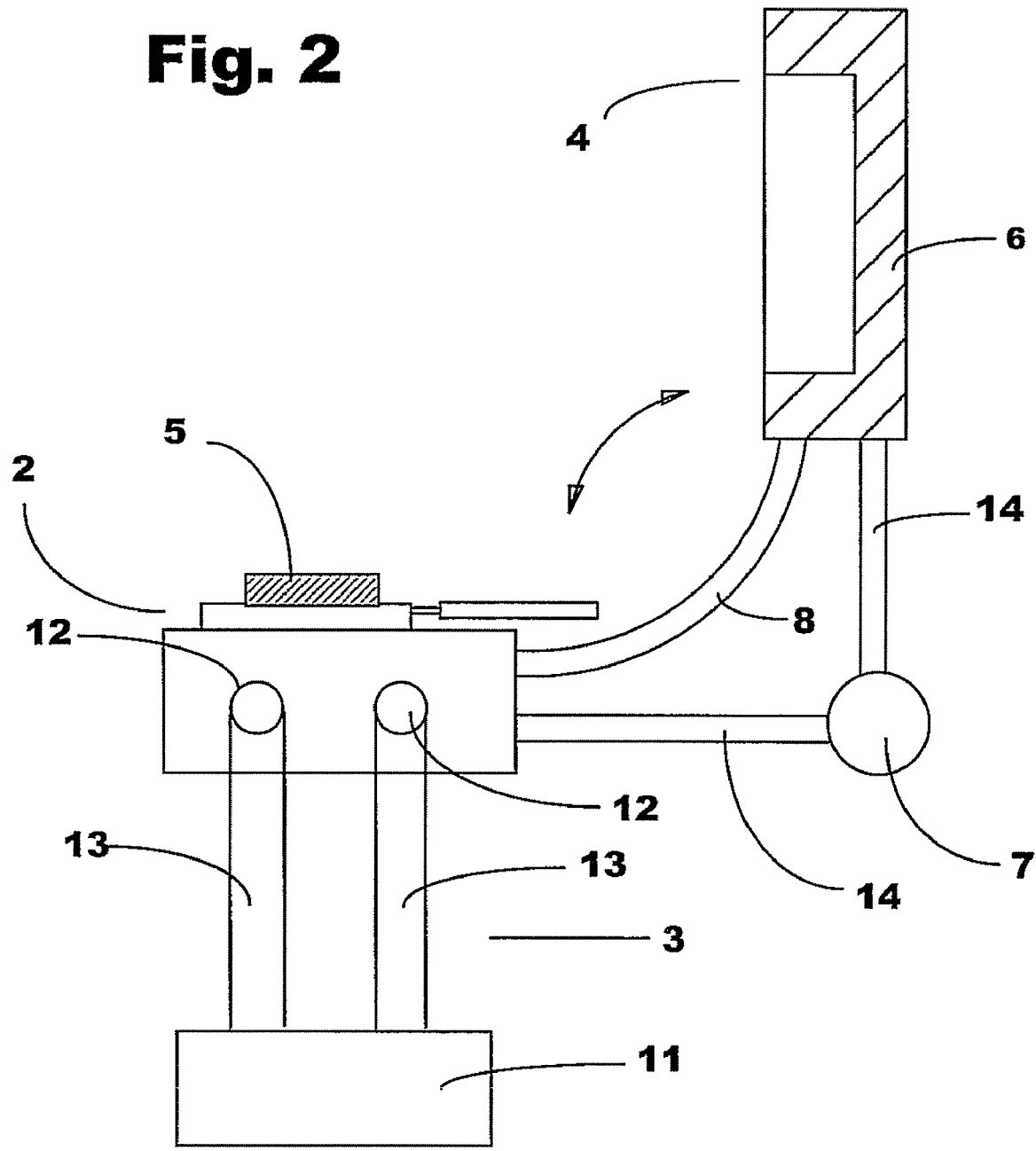
FIG. 2 is a view of the specimen holder with a thermal conduction plate.

Specimen holder 2 comprises two hose connectors 12 for connection to a refrigeration system (FIG. 2). A thermal conduction plate 4 having a frame 6 and a heat absorber is also arranged via a coolant line 14 on specimen holder 2, and pivotably mounted via a joint 7. In contrast to the rigidly embodied coolant line 14, a flexible coolant hose 8 is provided as a connection between specimen holder 2 and thermal conduction plate 4.

As a result of a connection of specimen holder 2 to a refrigeration system (not depicted here), coolant flows through both specimen holder 2 and thermal conduction plate 4, which are correspondingly cooled. After one or more sectioning operations, the heat present at the surface of specimen 5 can be removed using thermal conduction plate 4. For that purpose, thermal conduction plate is pivoted via joint 7 directly onto specimen 5, and good heat exchange is thereby ensured.

FIG. 2 is a view of specimen holder 2 with thermal conduction plate 4. Hose lines 13 that are connected to refrigeration system 11 are associated here with hose connectors 12 of specimen holder 2. Coolant circuit 3 is implemented via hose lines 13 to specimen holder 2 and from there via coolant hose 8 to thermal conduction plate 4, and from there via coolant line 14 back to specimen holder 2 and refrigeration system 11.

FIG. 3, like FIG. 2, shows specimen holder 2 and thermal conduction plate 4, although in this exemplifying embodiment the latter is not connected to the coolant circuit but instead has a Peltier element 15 associated with it for cooling. What is provided here as a connection between specimen holder 2 and thermal conduction plate 4 is a linkage 16 that is interrupted by joint 7. In this exemplifying embodiment thermal conduction plate 4 is electrically cooled, while specimen holder 2 is still connected to the coolant circuit.

PARTS LIST

1 Microtome
2 Specimen holder
3 Coolant circuit
4 Thermal conduction plate
5 Specimen
6 Frame with heat absorber
7 Joint
8 Coolant hose
9 Knife
10 Drive device
11 Refrigeration system
12 Hose connector
13 Hose line
14 Coolant line
15 Peltier element
16 Linkage

What is claimed is:

1. A microtome (1) comprising:
    a refrigeration system (11) having a coolant circuit (3);
    a specimen holder (2) for receiving a specimen, the specimen holder being connected to the coolant circuit (3) for cooling the specimen holder;
    a knife (9) for sectioning a specimen for subsequent microscopic examination; and
    a cooled thermal conduction plate (4) selectively positionable relative to the specimen holder to position the thermal conduction plate directly onto a surface of a specimen held by the specimen holder after the surface is exposed by a sectioning operation of the knife,
    wherein the specimen is positioned for sectioning by the knife and cooled by the thermal conduction plate while the specimen is held in the same position in the microtome.

2. The microtome (1) according to claim 1, wherein the thermal conduction plate (4) is connected to the coolant circuit (3) for cooling the thermal conduction plate.

3. The microtome (1) according to claim 2, wherein the thermal conduction plate (4) is connected via a coolant hose (8) to the specimen holder (2).

4. The microtome (1) according to claim 1, wherein the thermal conduction plate (4) is embodied as a Peltier element (15).

5. The microtome (1) according to claim 1, further comprising a Peltier element (15) connected to the thermal conduction plate (4) for cooling the thermal conduction plate.

6. The microtome (1) according to claim 1, wherein the thermal conduction plate (4) includes a frame (6) having a heat absorber.

7. The microtome (1) according to claim 6, wherein the thermal conduction plate (4) is made of a highly thermally conductive material.

8. The microtome (1) according to claim 7, wherein the thermal conduction plate (4) is made of chrome-plated brass.

9. The microtome (1) according to claim 1, wherein the thermal conduction plate (4) is has a round shape.

10. The microtome (1) according to claim 1, wherein the thermal conduction plate (4) is has a rectangular shape.

11. The microtome (1) according to claim 1, wherein the thermal conduction plate (4) is arranged on the microtome (1) or the specimen holder (2) pivotably via a joint (7).

12. The microtome (1) according to claim 1, wherein the refrigeration system (11) is part of a cryostat.

\* \* \* \* \*